United States Patent [19]

Halliburton

[11] Patent Number: 5,368,603
[45] Date of Patent: Nov. 29, 1994

[54] ENDARTERECTOMY CATHETER, AND METHOD OF USE THEREOF

[76] Inventor: Alexander G. Halliburton, 20 Coachman Terrace, Cloverbar Ranch, Edmonton, Canada, T8H 1M2

[21] Appl. No.: 533,402

[22] Filed: Jun. 5, 1990

[51] Int. Cl.$^5$ .......................................... A61M 25/00
[52] U.S. Cl. .................... 606/159; 606/17; 604/22
[58] Field of Search ............... 606/159, 170, 180, 171; 604/22; 128/751–755

[56] References Cited

U.S. PATENT DOCUMENTS

| | | | |
|---|---|---|---|
| 3,173,414 | 3/1965 | Guillant | 128/752 |
| 3,289,669 | 12/1966 | Dwyer et al. | 128/752 |
| 3,401,684 | 9/1968 | Dremann | 128/752 |
| 3,606,878 | 9/1971 | Kellogg, Jr. | 606/171 |
| 4,445,509 | 5/1984 | Auth | 128/305 |
| 4,616,648 | 10/1986 | Simpson | 128/303 |
| 4,669,469 | 6/1987 | Gifford, III et al. | 606/159 |
| 4,771,774 | 9/1988 | Simpson et al. | 128/305 |
| 4,781,186 | 11/1988 | Simpson et al. | 606/171 |
| 4,819,635 | 4/1989 | Shapiro | 606/170 |
| 4,994,067 | 2/1991 | Summers | 606/159 |

FOREIGN PATENT DOCUMENTS

| | | | |
|---|---|---|---|
| 352872A3 | 3/1985 | European Pat. Off. | A61B 17/22 |
| 0291170 | 11/1988 | European Pat. Off. | 606/159 |
| 2622850 | 9/1977 | Germany | 128/754 |
| 8905611 | 6/1989 | WIPO | 606/170 |

OTHER PUBLICATIONS

Altered Fluorescence Emission During Continuous Wave Laser Ablation of Atherosclerotic Plaque by Alexandra R. Lucas, Richard H. Clarke, Jeffrey M. Isner, 18 pages.

The Characterization of Human Coronary Artery Atherosclerotic Plaque Fluorescence Emission by Alexandra Lucas, Markus J. Radosavljevic, Erbin Lu, Edward J. Gaffney, 26 pages.

Correlation of Fluorescence Emission With the Plaque Content and Intimal Thickness of Atherosclerotic Coronary Arteries by Edward J. Gaffney, Richard H. Clarke, Alexandra R. Lucas, and Jeffrey M. Isner, from Lasers in Surgery and Medicine 9:215–228 (1989).

Article by Eric R. Bates, MD entitled Percutaneous Atherectomy Catheters, from Cardiology Clinis, Vo. 6, No. 3, Aug. 1988, pp. 373–382.

Laser Therapy for Cardiovascular Disease: Current Status and Future Direction by Jeffrey M. Isner, constance D. Fields, Alexandra R. Lucas, from Choices in Cardiology, vol. 2, No. 5, pp. 225–228.

Laser therapy in the treatment of cardiovascular disease by Jeffrey M. Isner, Alexandra R. Lucas, Constance D. Fields, from British Journal of Hospital Medicine, vol. 40, Sep. 1988, pp. 172–178.

*Primary Examiner*—C. Fred Rosenbaum
*Assistant Examiner*—William Lewis

[57] ABSTRACT

An endarterectomy catheter for removing obstructions from an artery comprises a cylindrical housing, the housing having an opening across which a primary shear is movable. The primary shear is razor sharp and cylindrical and movable by means of a cable and trigger backward and forward within the housing to excise obstructions that protrude into the opening. A guide wire positions the catheter in an artery.

The edge of the housing at the opening may be sharp to grip the obstruction and to assist in the cutting action of the primary shear. The shear is hollow and collects debris from the excised obstruction. Openings in the housing allow blood to pass through the body.

A method of removing obstructions from an artery includes locating a housing in an artery with an obstruction protruding into an opening in the housing, moving a razor sharp cylindrical shear across the opening to excise the obstruction, encapsulating the excised obstruction in the housing, and removing the housing from the artery.

15 Claims, 6 Drawing Sheets

ENDARTERECTOMY CATHETER, AND METHOD OF USE THEREOF

FIELD OF THE INVENTION

This invention relates to artherectomy catheters, and to a method of excising obstructions from an artery.

BACKGROUND OF THE INVENTION

An endarterectomy or atherectomy catheter is a device that is inserted in an artery to remove plaque from the walls of the arteries. This helps to decrease the risk of heart attacks. In medical terms, an endarterectomy catheter is a device used for the mechanical recannalization of occluded arteries. Occlusions of the vascular lumen may result from atherosclerotic lesions in human coronary arteries resulting in unstable angina and eventual myocardial infarction.

Several atherectomy catheters have been developed but all are relatively complicated and expensive devices.

Simpson, U.S. Pat. No. 4,781,186, describes a double chambered catheter with a rotating cutting blade. The distal end of the catheter consists of a solid cylindrical blade in a longitudinal housing with a longitudinal window over a third of its circumference. The window is on one side and a balloon is on the other side of the catheter. The housing and the rotating blade are made of stainless steel. The blade is attached to a torque cable in one of the catheter chambers. This chamber is also used to inject fluid or contrast media into the artery. The other chamber is used for balloon inflation. A short terminal fixed guide wire assists in positioning the window towards the atherosclerotic lesion. The cutting blade is then activated by a hand held motor at 2,000 rpm and the blade is rotated against the lesion. Excised plaque is trapped inside the catheter. A separate mechanism is used for balloon inflation. Other related patents for the Simpson atherectomy catheter are European application 352,872, U.S. Pat. Nos. 4,771,774; 4,669,649; and 4,616,648.

Auth, U.S. Pat. No. 4,445,509 describes a catheter having a rotating abrasive burr that can be advanced over a movable guide wire. The burr rotates at 150,000 rpm or higher and is driven by a compressed air turbine. The turbine also pumps a saline solution to cool the fast moving parts.

Theratek International of Miami, Fla., provides a single lumen flexible polyurethane catheter (also called the Kensey atherectomy catheter), having a rotating metallic cam at the distal end which is driven at 100,000 rpm to emulsify the targeted lesion.

Ultramed, Inc. of San Diego, Calif., provides a transluminal extraction endarterectomy catheter having a rotating steel cutting blade. The blade rotates at high speed, 750 rpm, to excise the targeted lesion. A vacuum is used to retrieve the debris from the lesion.

SUMMARY OF THE INVENTION

The inventor has provided a simplified catheter that does not require high speed rotating blades or drills, and a method of excising obstructions from an artery that may be carried out with the endarterectomy catheter. The atherectomy catheter of the present invention mechanically removes therosclerotic plaque by means of the shearing action of a blade or between a blade and an edge of a housing. Thus in one embodiment, there is provided an endarterectomy catheter for removing obstructions from an artery comprising:

a housing adapted for entry into the artery;

the housing including a forward end and a rearward end, and having an opening in the housing between the forward and rearward ends;

a primary shear disposed within the housing and movable backward and forward across the opening;

means connected to the primary shear and operable from outside the artery for moving the primary shear forward and backward; and means for locating the housing within the artery.

The endarterectomy catheter may further include means for collecting fragments of an obstruction that has been cut by the primary shear.

The endarterectomy catheter housing is preferably substantially cylindrical and the primary shear is preferably hollow, substantially cylindrical and snugly fitted within the housing to create, along with the edge of the opening, a pair of opposing shearing surfaces.

In a further embodiment, the endarterectomy catheter housing includes an inner tubular section extending from the forward end to the rearward end, and an outer tubular section extending from the forward end to the rearward end, the inner tubular section being fitted within the outer tubular section, and the primary shear being disposed between the inner tubular section and the outer tubular section.

In a still further embodiment, the opening extends fully around the housing.

In further embodiments, the forward edge of the opening, or all of the opening, may have a sharpened edge to assist in the guillotine action of the primary shear, the shear can be operated by a spring action, the housing may be flexible to allow for ease of positioning of the housing and the housing may be provided with openings in its forward and rearward ends to allow blood to flow through the catheter while it is in operation.

In one embodiment of the method of the invention, there is provided a method of excising an obstruction from an artery using a catheter having a housing adapted for entry into the artery, the housing including an outer section defining an opening, the size of the opening being selected to permit entry of at least part of the obstruction into the opening, a blade slidably disposed within the housing and movable reciprocally across the opening from a first position in which the opening is open to a second position in which the opening is closed by the blade, and means for reciprocally moving the blade, the method comprising:

locating the housing within the artery such that the obstruction is adjacent the opening;

moving the blade away from the opening so that at least part of the obstruction enters the opening;

moving the blade across the opening to excise at least part of the obstruction;

encapsulating the excised part of the obstruction within the housing; and removing the housing from the artery.

The advantages of using the catheter over the prior art devices include: the primary cutting edge cleaves the obstruction cleanly, leaving a smooth surface; there is no high speed rotating object in the artery that can otherwise damage the artery; there is no heat build up through operation of the cutting edge; no cooling mechanism is required; no vacuum is required to remove fragments of an obstruction and no motor or complex support system is required.

BRIEF DESCRIPTION OF THE DRAWINGS

There will now be described preferred embodiments of the invention, with reference to the drawings, by way of illustration, in which like numerals denote like elements and in which.

DESCRIPTION OF PREFERRED EMBODIMENTS

In this patent, a shear is the cutting means or blade used to cut through an obstruction using a cutting or slicing action. When a primary shear is used in conjunction with an opposing secondary shear, then the resulting scissors like action is referred to as a guillotine action.

Also, in this patent, the material that is sought to be removed from an artery (known for example as atherosclerotic plaque, atheroma or lesion), whether it be a fatty, fibrous or calcified tissue deposition, will be referred to as the obstruction.

A description of methods and apparatus currently used for the removal of obstructions may be found in the Textbook of Interventional Cardiology, Edited by E. J. Topol, Saunders, Philadelphia, 1990.

Physical Configuration

Preferred embodiments of the invention will now be described.

Figure 1:
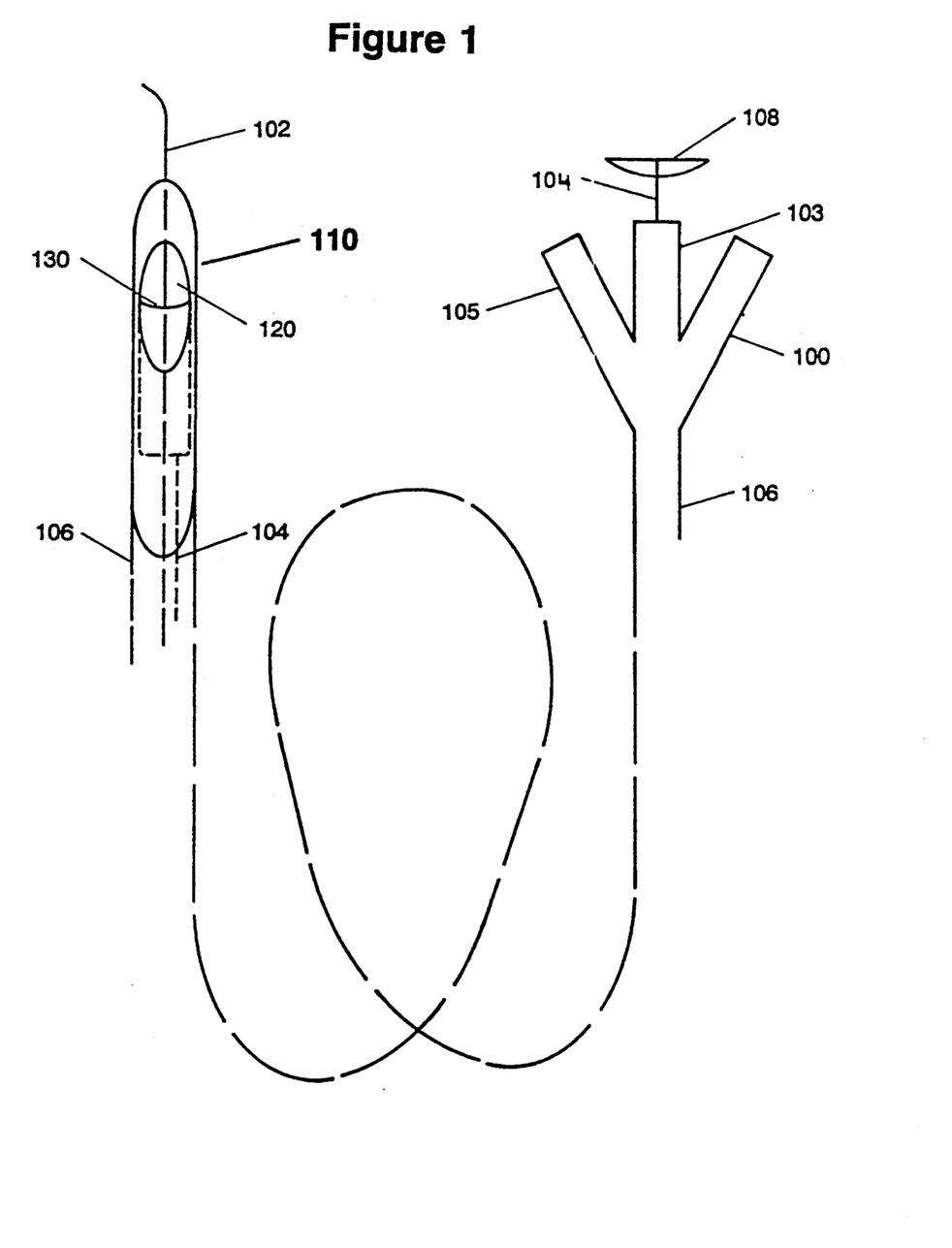
FIG. 1 is a perspective of an embodiment of a catheter according to the invention with a cable connection to the catheter.

Referring to FIG. 1, there is shown a perspective of a catheter according to the invention. A housing 110, including an opening 120 and primary shear or blade 130, is connected to means such as cable 104 for moving the primary shear 130 in the housing 110 across the opening 120. Means such as guide wire 102 for locating the housing 110 in an artery passes through the housing 110. Both the guide wire 102 and cable 104 are capable of sliding within at least one plastic sleeve 106. The opening 120 is oval, slightly elongated in the longitudinal direction, and should be sufficiently large to receive at least part and preferably all of an obstruction. The cable 104 is preferably operated manually from outside the artery by trigger 108 to move the primary shear 130 backward and forward (reciprocally) within the housing 110 across the opening 120. The guide wire 102 exits the plastic sleeve 106 at port 103, and the cable 104 exits the plastic sleeve at port 105. An injection port 100 for injecting die into the artery, to assist in locating the housing 110 within the artery, is also provided.

Three embodiments of the invention will be described here with reference to FIGS. 2A, 2B, 3A, 3B, 4A and 4B. In each case, the same guide wire 102 and cable 104 are used, together with plastic sleeve 106, trigger 108 and ports 100, 103 and 105. The main difference between the embodiments shown in these figures is the construction of the housing, the primary shear and the opening and these will be described in some detail.

Figure 2A:
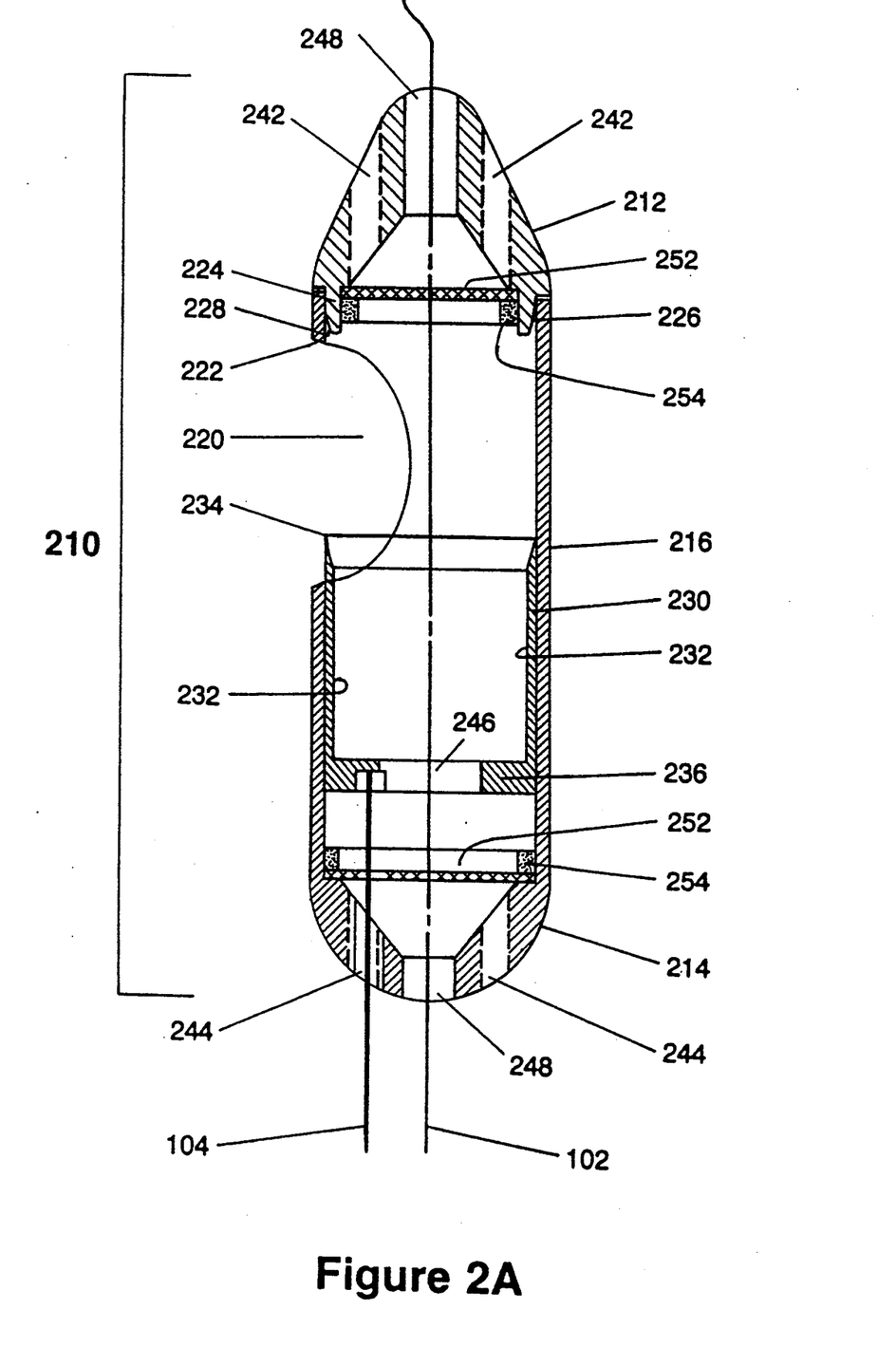
FIG. 2A is a longitudinal section of one embodiment of a housing according to the invention.
Figure 2B:
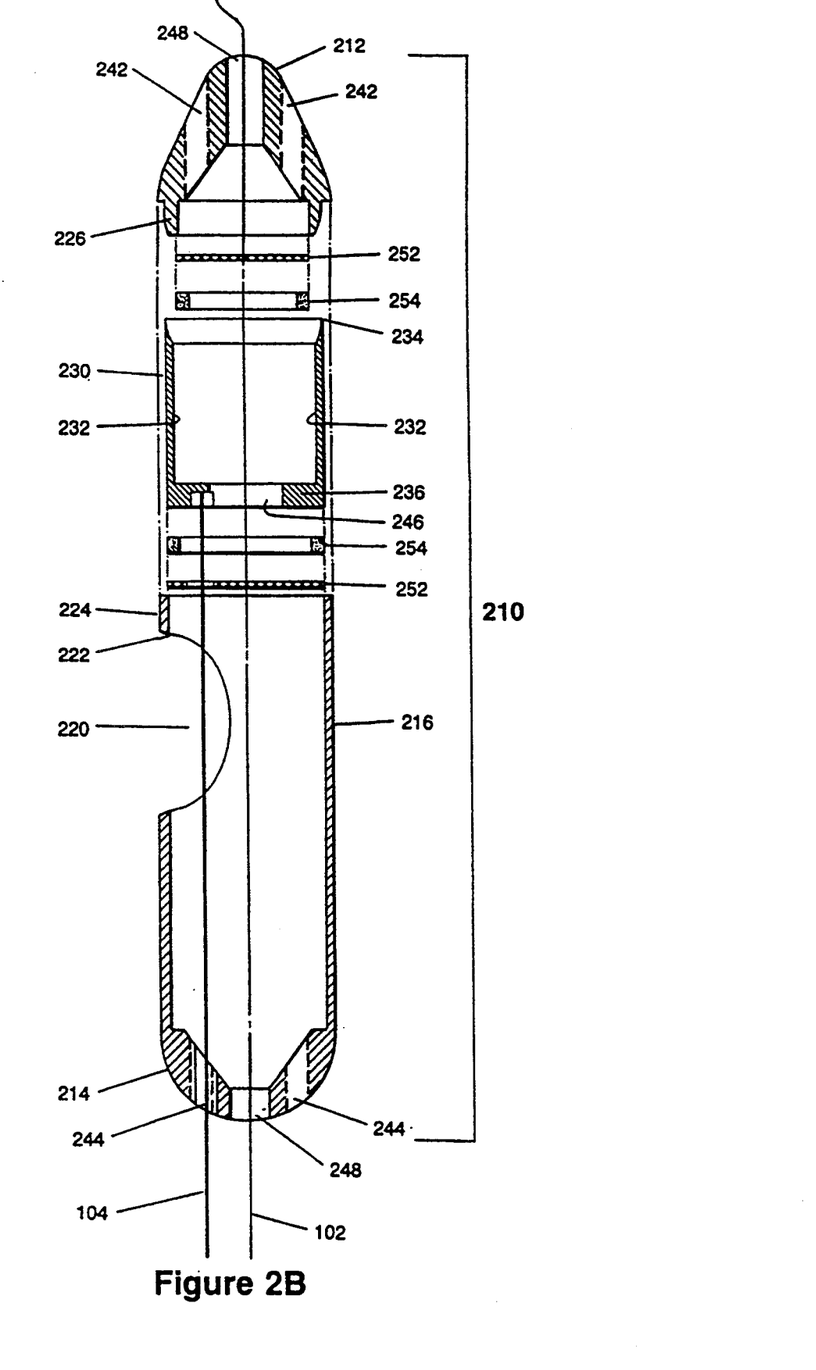
FIG. 2B is an exploded longitudinal section of the housing of FIG. 2A.

An embodiment of the catheter housing as shown in FIGS. 2A and 2B will now be described. Housing 210 includes a forward end cap 212 and a rearward end cap 214 connected by a tubular section 216. The tubular section 216 defines a substantially oval opening 220. Openings 242 and 244 in the forward and rearward ends respectively allow blood to pass through the housing 210. Guide wire 102 passes through openings 248 in the housing 210.

The primary shear 230 is hollow and substantially cylindrical with sides 232 and a cylindrical hollow ground cutting edge 234. The primary shear 230 is fitted snugly within the housing 210, and is movable backwards and forwards within the housing 210 across the opening 220 under control of the cable 104, which is attached by any suitable means to the rearward end 236 of the primary shear 230. At the forward extent of the primary shear 230 (upon movement of the primary shear 230 within the housing 210), the edge 234 is preferably sheathed within the housing 210 within the lip 224, and the opening 220 completely blocked by the cylindrical sides 232 of the primary shear 230. The primary shear 230 may be viewed as a circular blade that has been adapted to the shape of the housing, and sheathed within the housing, so that it is substantially only movable reciprocally across the opening, thus not requiring any rotary motion to excise the obstruction. The hollow, cylindrical interior of the blade constitutes means for collecting fragments of an obstruction and in operation encapsulates the excised part of the obstruction, thus facilitating removal of the excised part of the obstruction from the artery.

The cutting edge 234 of the primary shear 230 is preferably bevelled on the inside only as shown in FIGS. 2A and 2B, such that the cutting edge 234 is as close to the inside wall of the tubular section 216 as possible. The bevelled portion of the cutting edge 234 is preferably hollow ground (concave) to render the edge as sharp as possible, though it may be straight. For closer cutting, a second cutting edge (not shown) may be installed immediately adjacent the cutting edge 234. The cutting edge 234 may also be spiked to form a trocar like body with a point or spike, as described in more detail in relation to FIGS. 3A and 3B, such that the point may affix or spear the obstruction before piercing and excising it.

The cable 104 passes through one of the openings 244 in the rearward end 214 of the housing 210. The edge of the housing 210 that forms the boundary of the opening 220 at the forward end is preferably sharpened to form a secondary shear 222 to assist the cutting action of the primary shear 230. The secondary shear 222 assists particularly in holding the targeted obstruction in place while the sheer action of the primary shear 230 is responsible for most of the cutting action. The snug fit of the primary shear 230 within the housing 210 is important in creating an effective cutting surface close to the wall of the artery.

As shown in FIGS. 2A and 2B, an interior lip 226 is formed on the forward end cap 212 around the circumference of the housing 210 adjacent the secondary shear 222. The interior lip 226 and lip 224 provide a notch 228 into which the cutting edge 234 of the primary shear 230 snugly fits upon completion of the shearing action.

The close fit of the notch 228 with the cutting edge 234 helps to ensure that the obstruction is completely severed. This feature can be important in the case of some particularly resilient obstructions.

An opening 246 in the rearward end of the primary shear 230 allows blood to flow through the primary shear 230. Screens 252 may be provided in the forward and rearward end caps 212 and 214 respectively to catch any fragments of the obstruction that escape encapsulation by the primary shear 230. The screens 252 may be secured by lock washers 254 in end caps 212 and 214. If desired, the lock washers may be omitted and the screens 252 press fitted into place.

Figures 3A, 3B:
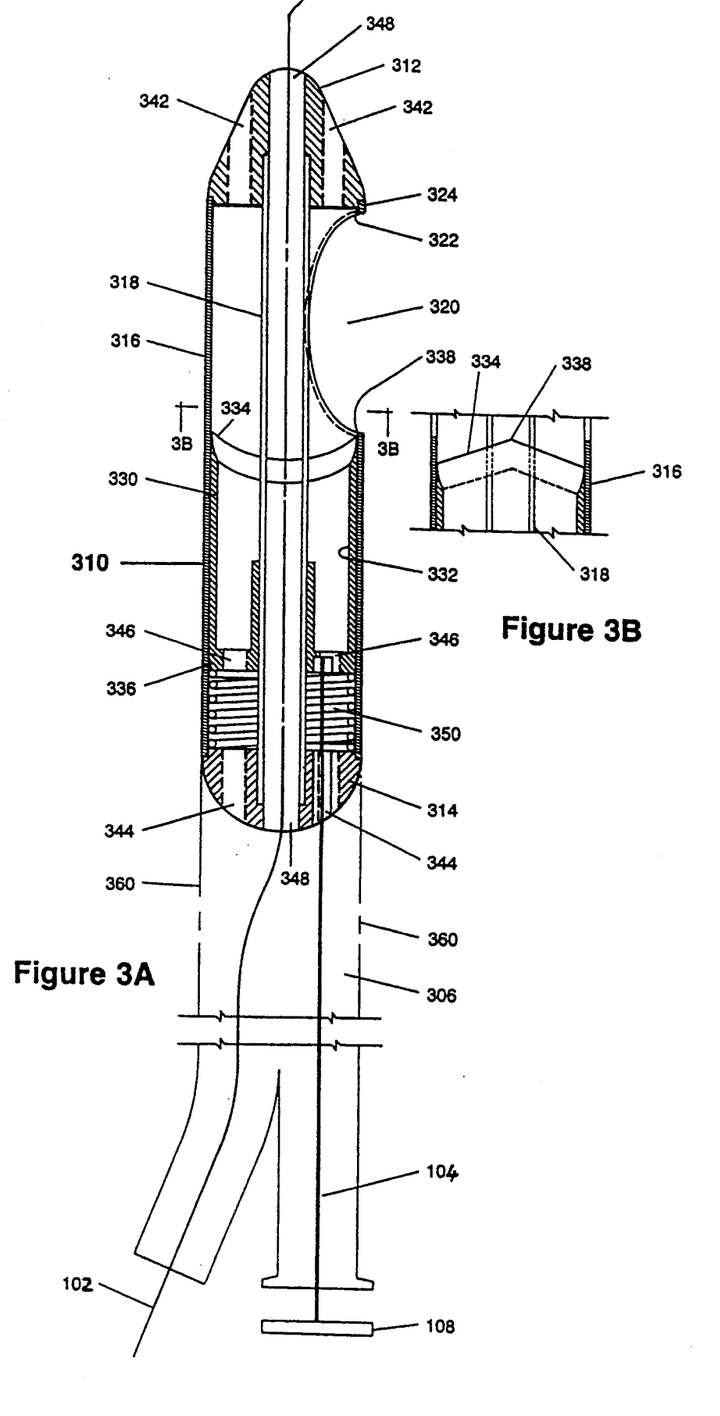
FIG. 3A is a longitudinal section of another embodiment of a housing according to the invention.
FIG. 3B is a section along the line 3—3 of FIG. 3A.

Referring to FIGS. 3A and 3B, there is shown a further embodiment of a catheter according to the invention. In this embodiment, the housing 310 is formed from a rearward end 314, a forward end 312, an outer tubular section 316 and an inner tubular section 318. The inner tubular section 318 is located centrally within the outer tubular section 316 and is hollow to allow blood to pass through the housing 310. Openings 342 and 344 in the forward and rearward ends respectively and the openings 348 at the rearward and forward ends of the inner tubular section 318 allow blood to pass through the housing 310. Guide wire 102 passes through openings 348 in the housing 310.

Although blood may pass through the embodiments of the housing shown, for most applications the catheter guide wire 102 and cable 104 combination sheathed within one or more plastic sleeves will be too thick to allow for the passage of blood during treatment. In such cases, autoperfusion methods as described at page 454 of the Textbook of Interventional Cardiology, referred to earlier in this patent, may be used to allow blood to flow during the use of the catheter. In such methods, small holes 360 are formed within the plastic sleeve 306 and the blood may pass into, along and out of the plastic sleeve 306.

The primary shear 330 slides along the inner tubular section 318 and is hollow and substantially cylindrical with sides 332 and rearward end 336. The rearward end 336 includes small openings 346 to allow blood to pass through the primary shear 330 while catching fragments of an obstruction, and is attached to the cable 102 for manipulation of the primary shear 330. The outer tubular section 316 defines an opening 320 surrounded by a lip 324. The opening 320 is formed similarly to the opening 220. The edge of the opening is sharpened, preferably hollow ground, to form a secondary shear 322.

Figure 4A:
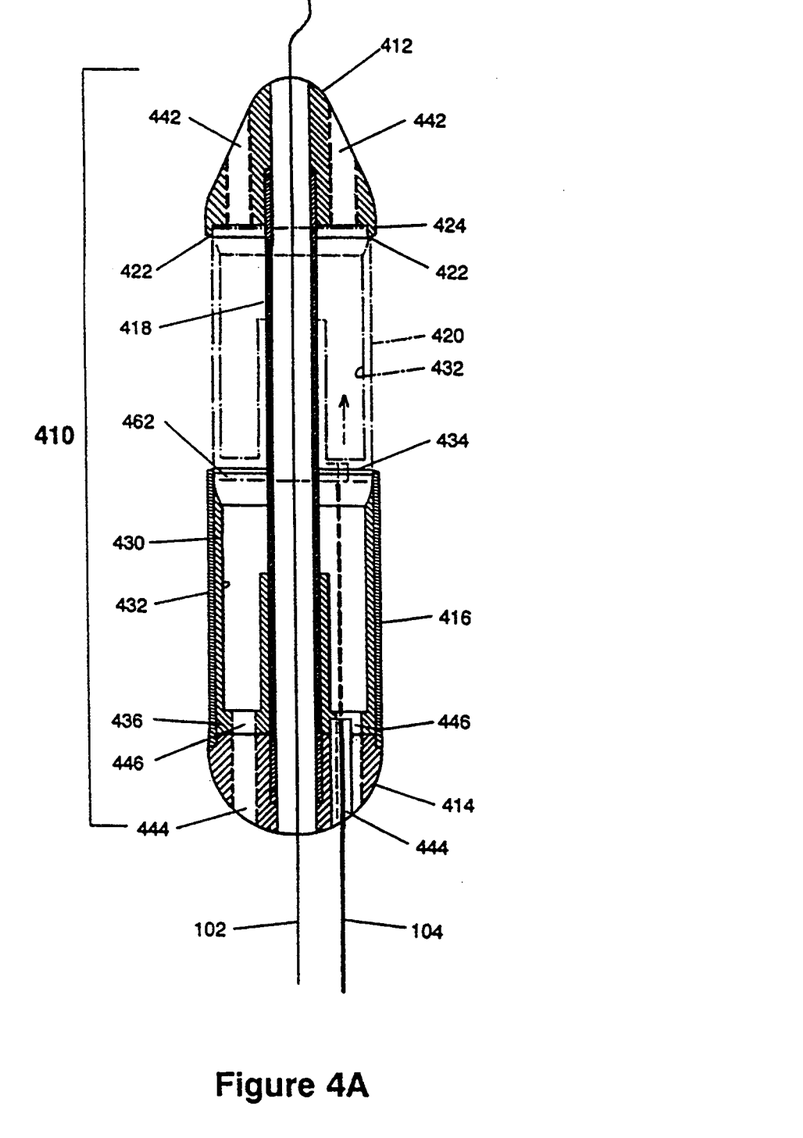
FIG. 4A is a longitudinal section of another embodiment of a housing according to the invention.

In this embodiment, a compression spring 350 is provided to urge the primary shear 330 forward from the position shown in FIG. 3A to a forward position (not shown, but the equivalent position is shown in ghost outline in FIG. 4A) in which the cutting edge 334 of the primary shear 330 is sheathed with the forward part of lip 324. A guillotine action occurs upon movement of the primary shear 330 into contact with the secondary shear 322, which will cleave and excise any obstruction protruding into the opening.

The primary shear 330 is sharpened in the radial direction to form an edge 334 for shearing an obstruction. The cutting edge 334 shown in FIGS. 3A and 3B also forms a point or spike 338 in the circumferential direction. The spike 338 may be formed on both sides of the primary shear 330, so that the spike 338 may be available for piercing even upon rotation of the primary shear 330 within the housing 310. If desired, the primary shear 330 and the tubular section 316 may be slotted or keyed (not shown) so that the primary shear 330 is guided linearly along the longitudinal axis of the tubular section 316 and prevented from rotating. The spring 350 may be operated using the cable 104 and a suitable catch on or near the trigger 108 for operating the cable 104. That is, the cable 104 may be pulled backward so that the primary shear 330 moves rearward in the housing 310 to compress the spring 350. The spring 350 may be held in place by a suitable catch and the catch released when it is desired to excise an obstruction. The catch may be any suitable catch for holding a compressed spring. For example, the catch may be a button on the cable 104 that slips into a recess in the plastic sheath 306 adjacent the trigger 308 when the trigger 308 is fully pulled back. To release the spring 350, the button is pushed in.

Figure 4B:
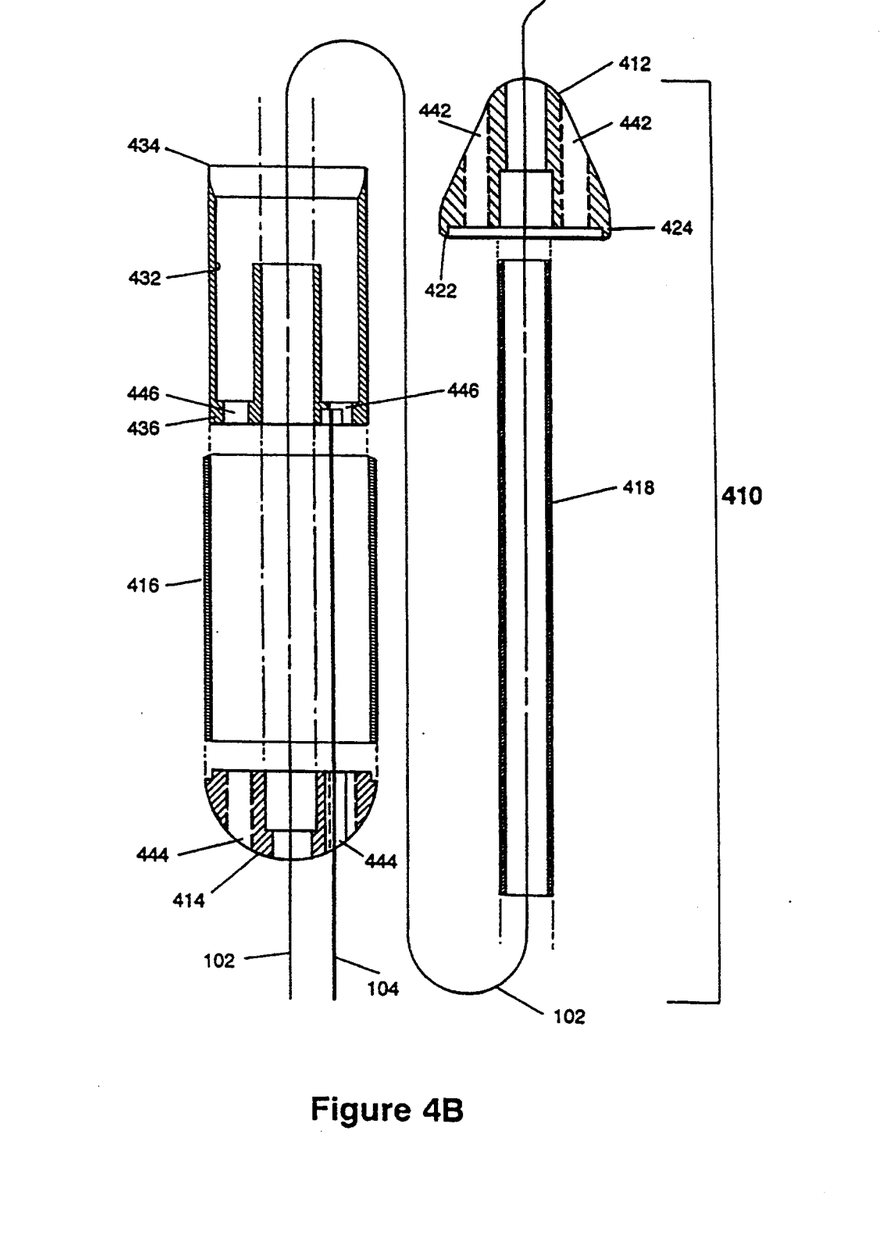
FIG. 4B is an exploded longitudinal section of the housing of FIG. 4B.

FIGS. 4A and 4B show a further embodiment of the invention, in which housing 410 includes rearward end cap 414, a forward end cap 412, an outer tubular section 416 and an inner tubular section 418. The outer tubular section 416 is concentrically located about the inner tubular section 418 and the inner tubular section 418 extends beyond the outer tubular section, thereby forming an opening 420 that extends fully around the housing 410 between the outer tubular section 416 and the forward end cap 412. The inner tubular section 418 is preferably hollow to allow for the insertion of the guide wire 102 and to allow for the passage of blood through the housing 410 during operation of the catheter. Openings 442 and 444 in the forward and rearward ends respectively allow blood to pass through the housing 410. As with the embodiment shown in FIGS. 3A and 3B, autoperfusion techniques may be required to allow blood to pass the plastic sleeve attached to the catheter.

Primary shear 430 is slidably mounted on the inner tubular section 418 and is movable from a first, rearward, position shown in FIG. 4A in which the primary shear 430 is fully retracted in the outer tubular section 416 to a second, forward, position shown in ghost outline in FIG. 4B. In the second position, the cylindrical side 432 of the primary shear 430 completely blocks the opening 420 and the cutting edge 434 of the primary shear 430 is sheathed in the lip 424 in the forward end cap 412 of the housing 410.

The primary shear 430 is hollow and substantially cylindrical with cylindrical sides 432 and sharp cutting edge 434 similar to the cutting edge described above in relation to FIGS. 2A and 2B. The primary shear 430 has one or more openings 446 in its rearward end 436 to allow blood to pass through the primary shear 430. The openings should preferably be sufficiently small to prevent excised parts of the obstruction from entering the blood stream.

The edge of the end cap 412 (at the lip 424) adjacent the opening 420 is preferably sharpened to form a secondary shear 422 to assist the shear action of the primary shear 430. The primary shear 430 is operated by the cable 104 which passes through an opening 444 in the rearward end cap 414 and connects to the primary shear 430 adjacent an opening 446 in the shear. The cable 104 in turn is operated by a trigger (not shown) but as described above in relation to FIGS. 1 and 3A. The secondary shear 422 may also be hollow ground as shown at 462 to create an extremely sharp cutting edge.

The primary shears 230, 330 and 430 are preferably made of stainless steel (for example by punching out an appropriate blank, and the edge formed by known sharpening techniques), although hard plastics, formed for example by injection moulding, may be satisfactory for cutting some kinds of obstruction. The sharpness of the primary shears should be selected to cut through the hardest obstruction that may be encountered, such as calcified plaque.

The housings 210, 310 and 410 may be made of stainless steel or suitable plastic, and for some applications may be made of flexible plastic. A flexible housing is desirable where the targeted artery is totally occluded or tortuous such that it would be difficult to penetrate with a rigid housing. Suitable plastics include high density polyurethane, methylpentane polymer, polyethylene tetraphthalate, chlortrifluoroethylene and polycarbonate. Plastics such as PLEXIGLAS (tm), available from Rohm & Haas Company of Pennsylvania, and DELRIN (tm) may also be used.

Each of the housings is preferably tapered and rounded at its forward end to facilitate insertion of the housing into an artery. The thickness of the housing should be chosen so that it is sufficiently strong to guide the primary shear and allow for insertion of the housing into an artery, but should not be so thick as to prevent the primary shear from cutting away a reasonable portion (preferably most) of the obstruction. The length of the housing may vary for most applications from 8–25 mm and the outside diameter may vary from 2–5 mm. The length of the shear may vary from 2–12 mm for most applications.

Manufacture of the end caps and tubular sections and their subsequent joining together may be accomplished by any of several known techniques commonly used for the manufacture of catheters for medical applications. A spring of an appropriate size and strength may be readily commercially obtained.

Operation of Preferred Embodiments

The catheter of the present invention is located in an artery according to known techniques. In this description, the general housing 110 is referred to, and except where specifically indicated, the housing 110 may have the design of housings 210, 310 or 410. The location of the targeted obstruction is first identified using known methods. To prevent damage to the artery while the housing 110 is being inserted into the artery, it is preferable that the primary shear 230, 330 or 430 be at the forward end of the housing 110, closing or blocking the opening or window with the cutting edge of the primary shear effectively sheathed within the housing 110.

Then, in the movable guide wire technique, a repetitive two step process is used. (1) The guide wire 102 is inserted slowly into the appropriate artery a short distance. (2) The housing 110, at the end of the cable 104, is then pushed manually along the guide wire 102, about the same distance. This process is repeated until the obstruction is reached.

Alternatively, in the fixed guide wire technique, the guide wire 102 may be attached to the housing 110 and the housing 110 fed into the artery until it reaches the obstruction.

In either case, at the obstruction, the housing 110 is oriented so that the obstruction is adjacent the opening 120 (or 220, 320 or 420 as the case may be) in the housing, and the primary shear is moved rearward to expose the opening and so that the obstruction at least partly (and preferably mostly) protrudes into the opening. In the case of particular obstructions and for example where the housing 110 is used, this could mean that substantially all of the obstruction may protrude into the opening, even where the obstruction extends all around the artery in the case of the opening 420. The trigger 108 may then be operated manually to move the primary shear forward in the housing 110 to excise the obstruction. The shearing action may be repeated if necessary to complete the excision of the obstruction.

In the case of the embodiment shown in FIGS. 3A and 3B, the cable 104 may be used to pull the primary shear 330 rearward to compress the spring 350, and then the cable 104 may be released so that the spring 350 urges the primary shear 330 forward in the housing 310 to excise the obstruction. The cable 104 may also be operated simultaneously with the spring 350 to assist the spring 350 (and vice versa).

The part of the obstruction that is excised by the primary shear then falls into the cylindrical body of the primary shear. Any debris may also be caught by the screens 252 (if present). If necessary the cutting action of the primary shear may be repeated to remove more of the obstruction.

The primary shear is then held in place within the housing while the catheter is withdrawn along the guide wire. The part of the obstruction that has been excised is thus encapsulated within the housing while the housing is removed from the artery. Once the catheter is removed from the artery, the obstruction may be removed from the housing and discarded or analyzed as desired. Since the catheter is designed to be simple and inexpensive, the catheter may also be discarded.

In some cases, where the obstruction does not protrude into the opening in the housing simply by placement of the housing adjacent the obstruction, it may be desirable to attach a conventional balloon (not shown) to one side of the housing, which may then be expanded using known techniques to force the housing against the wall of the artery near the obstruction so that the obstruction protrudes into the opening of the housing.

A person skilled in the art could make immaterial modifications to the invention described and claimed in this patent without departing from the essence of the invention.

Without intending to limit the generality of the statement in the last preceding paragraph, the catheter could be operated in reverse so that the cutting edge of the primary shear was at the rearward end of the primary shear. Thus the opening could also be oriented more to the rear of the housing. Thus it should be understood that the forward and rearward terminology in the claims may be reversed. However, this is not a preferred manner of operating the catheter. Alternatively, the primary shear could be given a degree of rotational movement across the opening but this complicates the operation of the catheter and is not preferred.

Also, the housing and the primary shear need not be cylindrical, although it is considered desirable that the housing have a cross-sectional shape that is similar to that of an artery.

It is important that the primary and secondary shears are sharp enough that they pierce the obstruction since otherwise they will simply push the obstruction out of the way and make it difficult to reach. Also, the cables used to operate the primary shear should be stiff enough to exert sufficient force on the primary shear to pierce the obstruction.

I claim:

1. An endarterectomy catheter for removing obstructions from an artery comprising:

a housing adapted for entry into the artery;

the housing including a forward end and a rearward end, and having an opening in the housing between the forward and rearward ends for receiving an obstruction;

a primary shear disposed within the housing and movable backward and forward across the opening;

a cable connected to the primary shear and operable from outside the artery for moving the primary shear forward and backward in the housing;

a spring for urging the primary shear forward to create a guillotine action upon movement of the primary shear; and means for locating the housing within the artery.

2. The endarterectomy catheter of claim 1 further including means for collecting fragments of an obstruction that has been cut by the primary shear.

3. The endarterectomy catheter of claim 1 in which the housing is substantially cylindrical and the primary shear is hollow, substantially cylindrical and snugly disposed within the housing, the primary shear having first and second ends.

4. The endarterectomy catheter of claim 3 in which the primary shear is substantially closed at the second end for collecting fragments of an obstruction that has been cut by the primary shear.

5. The endarterectomy catheter of claim 3 in which the opening is defined in the forward direction by a forward edge, and the forward edge is sharp to form a secondary shear.

6. The endarterectomy catheter of claim 3 in which the primary shear includes a cutting edge and the cutting edge forms at least one circumferential point.

7. An endarterectomy catheter for removing obstructions from an artery comprising:

a substantially cylindrical housing adapted for entry into the artery;

the housing including a forward end and a rearward end, and having an opening in the housing between the forward and rearward ends for receiving an obstruction;

a hollow, substantially cylindrical primary shear having first and second ends and snugly disposed within the housing and movable backward and forward across the opening;

means connected to the primary shear and operable from outside the artery for moving the primary shear forward and backward;

means for locating the housing within the artery; and the housing including an inner tubular section extending from the first end to the second end, and an outer tubular section extending from the first end, the inner tubular section being disposed within the outer tubular section, and the primary shear being disposed between the inner tubular section and the outer tubular section.

8. The endarterectomy catheter of claim 7 in which the inner tubular section is hollow and open at both of the forward and rearward ends of the housing, whereby blood may pass through the inner tubular section.

9. An endarterectomy catheter for removing obstructions from an artery comprising:

a substantially cylindrical housing adapted for entry into the artery;

the housing including a forward end and a rearward end, and having an opening in the housing between the forward and rearward ends for receiving an obstruction;

a hollow, substantially cylindrical primary shear having first and second ends and snugly disposed within the housing and movable backward and forward across the opening;

means connected to the primary shear and operable from outside the artery for moving the primary shear forward and backward;

means for locating the housing within the artery; and the housing including an inner tubular section extending from the forward end to the rearward end, and an outer tubular section extending from the rearward end partially towards the forward end so as to form an opening between the outer tubular section and the forward end, the opening extending around the housing, the inner tubular section being disposed within the outer tubular section, and the primary shear being disposed between the inner tubular section and the outer tubular section.

10. The endarterectomy catheter of claim 9 in which the opening is defined in the forward direction by a forward edge, and the forward edge is sharp to form a secondary shear.

11. The endarterectomy catheter of claim 10 further including a notch circumferentially formed around the forward end of the housing to receive the cutting edge of the primary shear.

12. An endarterectomy catheter for removing obstructions from an artery comprising:

a substantially cylindrical housing adapted for entry into the artery;

the housing including a forward end and a rearward end, and having an opening in the housing between the forward and rearward ends for receiving an obstruction;

a hollow, substantially cylindrical primary shear having first and second ends and snugly disposed within the housing and movable backward and forward across the opening;

means connected to the primary shear and operable from outside the artery for moving the primary shear forward and backward;

means for locating the housing within the artery; and spring means disposed within the housing for urging the shear forward.

13. The endarterectomy catheter of claim 12 in which the spring means is a compression spring disposed between the shear and the rearward end of the housing.

14. The endarterectomy catheter of claim 13 further including a catch for holding the spring under compression, and means for releasing the catch.

15. A method of excising an obstruction from an artery, the method comprising:

locating within the artery a housing having an opening in the housing such that the obstruction is adjacent the opening, the housing having a blade movable across the opening and initially blocking the opening;

moving the blade away from the opening so that at least part of the obstruction enters the opening;

urging the blade forward across the opening with a spring to excise at least part of the obstruction with a guillotine action;

encapsulating the excised part of the obstruction within the housing; and removing the housing from the artery.

* * * * *